United States Patent [19]
May et al.

[11] 4,196,057
[45] Apr. 1, 1980

[54] COLD END CORROSION RATE PROBE

[75] Inventors: Walter R. May, Des Peres; Michael J. Zetlmeisl, University City; David F. Laurence, Creve Coeur, all of Mo.

[73] Assignee: Petrolite Corporation, St. Louis, Mo.

[21] Appl. No.: 938,587

[22] Filed: Aug. 31, 1978

[51] Int. Cl.² ............ G01N 27/46; G01N 27/30
[52] U.S. Cl. .................. 204/1 T; 204/195 C; 324/65 CR
[58] Field of Search .......... 204/1 C, 195 C; 73/86; 324/29, 30 R, 30 B, 65 R, 65 CR; 422/53

[56] References Cited

U.S. PATENT DOCUMENTS

| | | | |
|---|---|---|---|
| 3,406,101 | 10/1968 | Kilpatrick | 204/1 |
| 3,627,493 | 12/1971 | Manley | 422/53 |
| 3,861,876 | 1/1975 | Robertson et al. | 23/230 C |
| 3,960,496 | 6/1976 | Schieber | 23/253 C |
| 3,980,542 | 9/1976 | Winslow, Jr. et al. | 204/195 C |
| 3,982,177 | 9/1976 | Walker et al. | 324/13 |
| 3,996,124 | 12/1976 | Eaton et al. | 204/195 C |
| 4,098,662 | 7/1978 | Schell et al. | 204/195 C |

OTHER PUBLICATIONS

Shields, "Boilers", F. W. Dodge Corp., N.Y., 1961, pp. 271-274 and 293-294.
G. R. Peacock "The Land Dewpoint Meter Uses an Old Principle to Provide New Measurements in Waste & Process Gases" paper presented at Conference of Instrument Society of America, Oct. 1976, pp. 1-10.
G. R. Peacock, "Methods of Measuring Sulfuric Acid Dewpoint," paper presented at 23rd Annual Instrument Society of America Analysis Symposium, May 1977.
Palmer & Beer, "Combustion Technology", Academic Press, N.Y., 1974, pp. 50-59.

Primary Examiner—Aaron Weisstuch
Attorney, Agent, or Firm—Sidney B. Ring; Hyman F. Glass

[57] ABSTRACT

A cold end corrosion rate measuring probe consisting of a corrosion rate meter probe modified by the addition of a cooling jacket and a temperature measuring device such as a thermocouple. The probe is adapted to be flush mounted in an exhaust line or flue. A coolant, e.g. water, is circulated through the jacket to bring monitored gas to its dew point, at which point, a corrosion rate measurement can be made. The dew point may also be indicated by increased conductivity across two adjacent electrodes of the probe, e.g., the reference and test electrodes. Measurement of corrosion rate and accompanying dew point can be correlated with sulfur trioxide concentration in flue or exhaust gases and hence enables predictability of occurrence and location of "cold end" corrosion, which also indicates inhibitor effectiveness.

10 Claims, 4 Drawing Figures

COLD END CORROSION RATE PROBE

BACKGROUND OF THE INVENTION

This invention relates to an apparatus and method for measuring cold end corrosion and dew point and more particularly to a flush mounted probe and its use in determining the cold end corrosion rate and dew point of an engine or gas turbine exhaust or flue gas. Measurement of dew point permits semi-quantitative determination of sulfur trioxide concentration in such gases and hence predictability of occurrence and location of so-called "cold end" corrosion, which also indicates inhibitor effectiveness. Measurement of corrosion rate identifies the problem, predicts severity and evaluates additive and operating performance.

When a sulfur containing fuel is employed in furnaces, engines such as Diesel engines, and gas turbines, corrosion occurs in the so-called "cold end" of the exhaust line or flue. For example, flue gases may contact relativey cold metal surfaces such as preheaters where the heat of the gas is recovered to preheat furnace air.

The gases contain water vapor and components, including sulfur trioxide, which are soluble in water to form corrosive solutions, i.e., electrolytes. When the dew point of such solutions is reached, such solutions, e.g. sulfuric acid, condense on the metal parts, causing corrosion.

This corrosion can of course be controlled by using corrosion inhibiting fuel additives, but such procedures vary in effectiveness. It has been proposed to determine the corrosion rate in a flue gas system and to evaluate the corrosion control treatment by employing a probe. See Schieber U.S. Pat No. 3,960,496, granted June 1, 1976.

The problem of cold end corrosion in the flues of stationary engines due to sulfuric acid condensation ($SO_3$ in $H_2O$) at relatively high temperatures (300°–400° F.) has had fuel additives such as magnesium presented for its solution for some time. The measurement of the onset of conductivity as temperature is lowered in so-called dew-point probes has been taken as an indication of the success or failure of a particular treatment. As less and less $SO_3$ is formed in the flue gas the point of condensation approaches the boiling point of pure water. The use of point of condensation as the sole indication of the amount of $SO_3$ ignores the possibility of probe poisoning and erroneous readings owing to irrelevant impurities in the gas stream as well as the possible absence of equilibrium.

Our invention allows the user to measure directly the phenomenon of interest, i.e. corrosion of the flue wall. We can make this measurement at or below the so called dew point and as long as we compare readings at similar conditions we can draw safe conclusions.

It is conceivable that an additive treatment might do little to change $SO_3$ content in the bulk gas stream, but might render it an ineffective corrosion agent at a metal surface. Dew point measurements alone (assuming that the probe is working and we are at equilibrium, etc.) could lead to the conclusion that an additive program is not working whereas corrosion measurements would give the correct data. It is not always (in fact it hardly ever is) a safe assumption to say that the microcosm of the surface above such a metal or above the metal and beneath a powdery deposit is the same as the bulk gas stream. To best study corrosion, we look at surfaces.

Further background on the problems of corrosion caused by flue gas and the significance of the sulfuric acid dew point may be found in the work by C. D. Shields, entitled "Boilers: Types, Characteristics and Functions" (F. W. Dodge Corp., New York, 1961), specifically on pages 271-274 and 293-294; and the work edited by H. B. Palmer and J. M. Beer, entitled "Combustion Technology" (Academic Press, New York, 1974), specifically on pages 50–59 (from Chapter II by W. T. Reid).

The cold end corrosion probe of the present invention provides the art with a simple means for monitoring the corrosivity of the exhaust or flue gases and the effectiveness of the corrosion inhibitors by means of dew point measurements coupled with actual corrosion rate measurements, such measurements enabling a semi-quantitative determination of the sulfur trioxide concentration in the gases. Such measurements also enable the prediction of the specific part of the system in which "cold end" corrosion will occur.

It is accordingly an object of the present invention to provide a cold end corrosion probe adapted for use in an exhaust line or flue system.

A further object of the invention is to provide a method for measuring the dew point of a gas or vapor containing water vapor and components which dissolve in water to form electrolytes.

Other objects, features and advantages of the present invention will be apparent from the following description.

SUMMARY OF THE INVENTION

The above and other objects of the invention are achieved by providing a cold end corrosion probe adapted to be flush mounted in an exhaust line, such as that from a Diesel engine or gas turbine, or a flue, such as that from a boiler furnace. The probe comprises a probe body supporting a cylindrical matrix of heat resistant, electrically insulating material, suitably a ceramic material, having embedded therein a center pin-type reference electrode, an annular test electrode and an annular auxiliary electrode arranged concentrically around the center reference electrode with the longitudinal axes of all the electrodes being in alignment and the end faces of the electrodes being flush with the end face of the matrix. Also supported on the probe body are electrical terminal means. Separate electrically conductive means extend through the probe body, connected, respectivey, at one end, to the reference electrode, the test electrode and the auxiliary electrode, and at the other end to the terminal means. The probe body is surrounded in a fluid tight manner by jacket means adapted to allow the end faces of the matrix and embedded electrodes to be exposed. The probe also includes means for bringing cooling fluid into heat exchange relationship with the matrix and embedded electrodes and means for measuring the temperature of the matrix and electrodes. The former may include cooling fluid inlet means and cooling fluid outlet means supported by the probe body and means for circulating such fluid through the jacket means. The temperature measuring means may include a thermocouple.

In addition to using the probe for direct corrosion rate measurements at or below the dew point of the exhaust or flue gases being monitored, the probe may be employed for dew point determinations either by noting the point at which a corrosion rate is first measured or by conductivity measurements, in which the dew point is indicated by increased conductivity across two electrodes of the probes. The probe may be connected separately or simultaneously to electrical means for measuring corrosion rate and electrical means for making conductivity measurements.

An aspect of the invention is a method of measuring the dew point of a gas or vapor containing water vapor and components which dissolve in water to form electrolytes. Such method involves exposing to such gas or vapor the end face of a heat resistant, electrically insulating matrix and the end faces of three electrodes embedded therein so that they are insulated from each other and have their end faces flush with the end face of the matrix. The elctrodes are electrically connected to electrical means for measuring conductivity and/or corrosion rate. The matrix and embedded electrodes are then cooled by heat transfer to a cooling fluid until a conductivity between two adjacent electrodes and/or a corrosion rate is measured. At this point, the temperature of the matrix with the embedded electrodes is measured. This is the dew point. In the preferred embodiment of the method, a probe wherein three concentric electrodes are embedded in the matrix is employed. These electrodes are a reference electrode, a test electrode and an auxiliary electrode. These electrodes may be connected to electrical means for measuring corrosion rate and/or two adjacent electrodes may be connected to electrical means for measuring conductivity. The process is particularly useful for measuring the dew point of a furnace flue gas or engine or gas turbine exhaust gas which contains sulfur trioxide, in which case the dew point measured is the sulfuric acid dew point. The probe should be positioned in the exhaust line or flue at a point where the gases are still above the dew point temperature.

Means for measuring corrosion rate using three electrode systems (reference, test and auxiliary electrodes) are known in the art. See, for example, Kilpatrick U.S. Pat. No. 3,406,101, granted Oct. 15, 1968. Corrosion rate instruments marketed by the Petrolite Corporation employ such systems, the technique involved being referred to as the PAIR (polarization admittance instantaneous rate) technique. An automatically zeroing instrument of this type facilitates the data gathering.

Steel is the preferred material for the reference electrode, although the theory of the technique indicates that other metals and metal alloys, e.g. cooper, brass, lead, nickel, etc., may be used under similar conditions. The use of a separate steel reference electrode, especially when the test electrode is steel, is advantageous, however, in that it permits use of the probe at high temperatures and pressures. As pointed out by Kilpatrick, above referred to, the difficulties normally encountered when taking potential measurements with a metal reference electrode are eliminated by using a test specimen and reference electrode of the same material regardless of the metal used. Neither the auxiliary electrode nor the reference electrode need be made of steel, or even of the metallic material required for the test electrode, but merely need to be conductive. The test electrode must be of a metallic material having polarization characteristics for measuring potential.

DESCRIPTION OF THE DRAWINGS

The details of the present invention may be more easily understood by reference to the appended drawings, of which.

Figure 1:
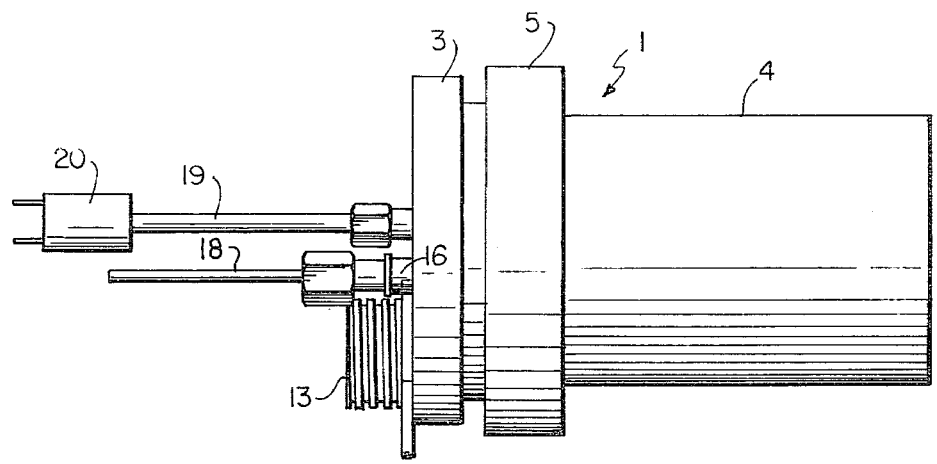
FIG. 1 is a side view of a specific embodiment of the cold end corrosion and dew point probe.
Figure 2:
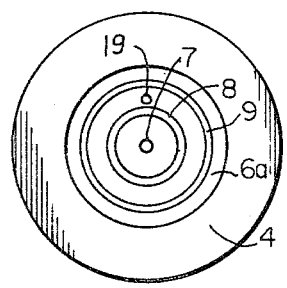
FIG. 2 is a top (electrode side up) view of the cold end corrosion and dew point probe.
Figure 3:
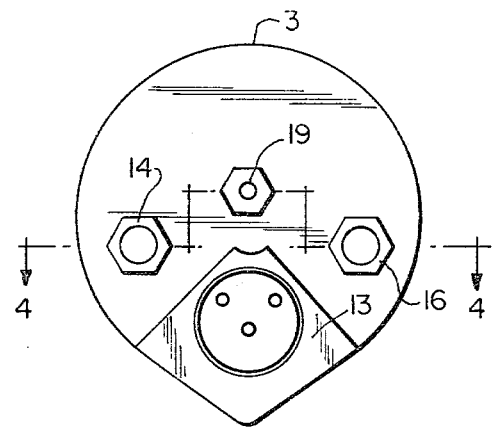
FIG. 3 is a bottom view of the cold end corrosion and dew point probe
Figure 4:
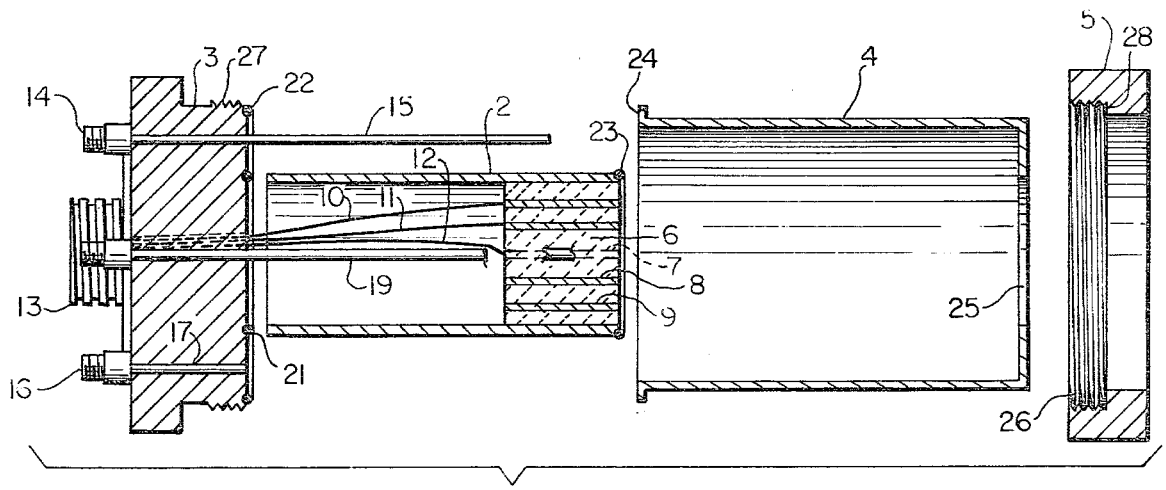
FIG. 4 is an exploded sectional view taken along the line 4—4 of FIG. 3, showing the main elements of the cold end corrosion and dew point probe.

The terms "top" and "bottom" used with reference to FIGS. 2 and 3, respectively, refer to the orientation in which the probe is commonly employed, which is vertical and not horizontal, as shown for convenience in FIGS. 1 and 4 of the drawings.

DESCRIPTION OF SPECIFIC EMBODIMENT

Referring to the drawing figures, the cold end corrosion probe, generally designated by the numeral 1, consists of a cylindrical housing 2, a base 3, a cylindrical jacket 4 and a nut 5, together with their associated structures and wiring. Housing 2, base 3, jacket 4 and nut 5 are suitably made of 316 stainless steel or a similar alloy, as are all other metal parts, to avoid the problem of corrosion of the probe. Jacket 4 is provided with a flange 24, which is secured to base 3 by means of nut 5, which is provided with threads 26 to engage threads 27 on base 3, and which has a circular shoulder 28 which is in contact with flange 24 when the nut is fastened. The bottom of jacket 4 is provided with a circular opening 25 of slightly smaller diameter than the housing 2. The lengths of the housing 2 and jacket 4 are such that the housing will be secured to the base along with the jacket when nut 5 is fastened. Fluid tight connection of housing 2 with base 3 is provided by rubber O-ring 21; of base 3 with the flange 24 of jacket 4 by rubber O-ring 22; and of housing 2 with jacket 4 by rubber O-ring 23.

The upper portion of the housing 2 surrounds a cylindrical ceramic matrix 6, which has embedded therein a center pin-type reference electrode 7, a test electrode 8 and an auxilliary electrode 9, concentrically arranged, the end faces of the electrodes being flush with the end face 6a of the matrix. When the probe is assembled by fastening nut 5, the end face 6a and the electrodees 7, 8 and 9 will be exposed through opening 25 of jacket 4. Electrical leads 10, 11 and 12 are connected, respectively, to electrodes 7, 8 and 9 at their other ends to an electrical terminal 13, which serves as a PAIR meter connector. Water inlet 14 and tube 15 provide for the admission of cooling water into the jacket and tube 17 and water outlet 16 provide for its withdrawal, thus providing circulation of water through jacket 4 around housing 2. Water inlet 14 and water outlet 16 may suitably be ¼" Swagelok tube fittings. A water supply conduit 18 is shown connected to water inlet 14 and a conduit for water withdrawal, not shown, may similarly be connected to water outlet 16. A thermocouple 19 is shown extending through the housing 2 and the matrix 6 and terminating at its other end at an electrical connector 20, adapted to be connected to an appropriate meter for reading temperatures. Base 3 is preferably of solid construction as shown in FIG. 4, with passageways provided for tubes 15 and 16, thermocouple 19 and electrical leads 10, 11 and 12.

The dew point is measured by inserting the probe in the exhaust or flue gas stream and allowing the probe surface (the end faces of the electrodes and matrix) to approximate the exhaust or flue gas temperature. The coolant (water or air) is passed through Jacket 4 until a corrosion rate is measured on a PAIR meter or a conductivity across two adjacent electrodes (e.g. the reference 7 and test 8 electrodes) is found with a conductivity meter. When this occurs, acid has condensed on the probe surface completing the electric circuit. The temperature at this time is the dew point.

The present probe is intended to be flush mounted in the exhaust line or flue. Thus, the probe may be made compatible with standard fittings for allowing instrument access to pipe interiors. Among such fittings are Cosasco's nominal two inch fittings and T. D. Williamson's two inch fittings. (Examples of prior art Petrolite instruments compatible with such fittings are, respectively, the M-555-E Cosasco Compatible Flush-Mounted probe and the M-540-E Flush-Mounted probe. Among the patents dealing with flush mounting of corrosion probes are U.S. Pat No. 3,980,542 to Winsow and Mayse and U.S. Pat. No. 3,996,124 to Eaton and Annand.)

The PAIR meter above referred to contains the electronic circuitry and gauges required for applying the PAIR technique as described in the above mentioned Kilpatrick patent and elsewhere.

Measurement of dew point enables a semi-quantitative determination of the sulfur trioxide concentration in the exhaust or flue gas, predicts the part of the system in which "cold end" corrosion will occur and gives an indication of the effectiveness or additives. In addition, the inherent corrosion rate measurement indicates the degree of inhibition of an additive such as magnesium and the actual condition at the surface.

In utilizing the dew point information obtained by the use of the probe, as above described, use may be made of known data correlating sulfuric acid or sulfur trioxide concentration in flue gas with the acid dew point. Such data is graphically presented in the above referred to work by Shields, page 272 and Palmer and Beer, page 54.

Various changes and modifications may be made to the structure of the present probe and the method of its use without departing from the spirit of the invention. It is intended that the present description be taken in illustration of the invention, and the appended claims define the scope thereof.

We claim:

1. A cold end corrosion probe adapted to be flush mounted in an exhaust line or flue, said probe comprising:
   (a) a center pin-type reference electrode;
   (b) an annular test electrode and an annular auxiliary electrode arranged concentrically around said center pin-type reference electrode;
   (c) a cylindrical matrix of heat resistant, electrically insulating material, said reference, test and auxiliary electrodes being embedded in said matrix with the longitudinal axes in alignment and the end faces of the electrodes being flush with the end face of the matrix;
   (d) a probe body, said probe body supporting said matrix with said embedded electrodes;
   (e) electrical terminal means supported by said probe body ;
   (f) separate electrical conductive means extending through said probe body and connected, respectively, at one end, to said reference electrode, said test electrode and said auxiliary electrode, and at the other end to said electrical terminal means;
   (g) jacket means surrounding said probe body in a fluid-tight manner, said jacket means being adapted to allow said end face of said matrix and said end faces of said embedded electrodes to be exposed;
   (h) means for bringing cooling fluid into heat exchange relationship with said matrix with said embedded electrodes; and
   (i) means for measuring the temperature at said end face of the matrix.

2. A cold end corrosion probe as defined in claim 1, wherein said means (h) for bringing cooling fluid into heat exchange relationship with said matrix with said embedded electrodes comprises cooling fluid inlet means and cooling fluid outlet means supported by said probe body (d) and means for circulating said fluid through said jacket means (g).

3. A cold end corrosion probe as defined in claim 1, wherein said means (i) for measuring the temperature of said matrix with said embedded electrodes comprises a thermocouple.

4. A cold end corrosion probe as defined in claim 1 wherein said cylindrical matrix of heat resistant insulating material (c) is composed of ceramic material.

5. A process for measuring the dew point and corrosivity of a gas or vapor containing water vapor and components which dissolve in water to form electrolytes, comprising exposing the end face of a heat resistant, electrically insulating matrix and the end faces of three electrodes embedded therein so that they are insulated from each other and have end faces flush with the end face of said matrix, to said gas or vapor, said electrodes being a reference electrode, a test electrode and an auxiliary electrode, said electrodes being electrically connected to electrical means for measuring corrosion rate; cooling said matrix and embedded electrodes by heat transfer to a cooling fluid until a corrosion rate is measured; and measuring the temperature of said matrix and embedded electrodes when such corrosion rate is measured.

6. The process of claim 5 wherein the electrodes embedded in said heat resistant, electrically insulating matrix, are concentrically arranged.

7. The process of claim 5, wherein two adjacent said electrodes are also connected to electrical means for measuring conductivity.

8. The process of claim 3 wherein said gas or vapor containing water vapor and components which dissolve in water to form electrolytes is a flue gas containing sulfur trioxide and the dew point measured in the sulfuric acid dew point.

9. The process of claim 7 wherein said gas or vapor contaning water vapor and components which dissolve in water to form electrolytes is an exhaust gas from an engine or a gas turbine containing sulfur trioxide and the dew point measured is the sulfuric acid dew point.

10. A cold end corrosion probe as defined in claim 1, wherein said reference, test and auxiliary electrodes are connected, via said electrical terminal means, to electrical means for measuring corrosion rate.

* * * * *